(12) United States Patent
Baque et al.

(10) Patent No.: US 8,044,205 B2
(45) Date of Patent: Oct. 25, 2011

(54) PROCESS FOR MANUFACTURING 3(R)-(2-HYDROXY-2,2-DITHIEN-2-YLACETOXY)-1-(3-PHENOXYPROPYL)-1-AZONIABICYCLO[2.2.2]OCTANE BROMIDE

(75) Inventors: Nuria Busquets Baque, Barcelona (ES); Francesca Pajuelo Lorenzo, El Prat de Llobregat (ES)

(73) Assignee: Laboratorios Almirall, S.A., Barcelona (ES)

( * ) Notice: Subject to any disclaimer, the term of this patent is extended or adjusted under 35 U.S.C. 154(b) by 96 days.

(21) Appl. No.: 12/374,185

(22) PCT Filed: Jul. 16, 2007

(86) PCT No.: PCT/EP2007/006278
§ 371 (c)(1),
(2), (4) Date: Feb. 11, 2009

(87) PCT Pub. No.: WO2008/009397
PCT Pub. Date: Jan. 24, 2008

(65) Prior Publication Data
US 2009/0299042 A1    Dec. 3, 2009

(30) Foreign Application Priority Data
Jul. 21, 2006  (ES) .................................. 200601951

(51) Int. Cl.
*C07D 453/02*  (2006.01)
(52) U.S. Cl. ...................................................... 546/137
(58) Field of Classification Search .................... 540/477
See application file for complete search history.

(56) References Cited

U.S. PATENT DOCUMENTS

| | | |
|---|---|---|
| 3,714,357 A | 1/1973 | Houilles et al. |
| 4,224,332 A | 9/1980 | Gueremy et al. |
| 4,579,854 A | 4/1986 | Iwakuma et al. |
| 4,644,033 A | 2/1987 | Gnanou et al. |
| 4,675,326 A | 6/1987 | Amitai et al. |
| 4,843,074 A | 6/1989 | Rzeszotarski et al. |
| 5,201,308 A | 4/1993 | Newhouse |
| 5,435,301 A | 7/1995 | Herold et al. |
| 5,610,163 A | 3/1997 | Banholzer et al. |
| 5,654,314 A | 8/1997 | Banholzer et al. |
| 6,455,524 B1 | 9/2002 | Bozung et al. |
| 6,475,467 B1 | 11/2002 | Keller et al. |
| 6,537,524 B1 | 3/2003 | Hassan et al. |
| 6,608,054 B2 | 8/2003 | Meade et al. |
| 6,620,438 B2 | 9/2003 | Pairet et al. |
| 6,686,346 B2 | 2/2004 | Nilsson et al. |
| 6,696,042 B2 | 2/2004 | Pairet et al. |
| 6,750,226 B2 | 6/2004 | Forner et al. |
| 6,890,517 B2 | 5/2005 | Drechsel et al. |
| 7,078,412 B2 | 7/2006 | Fernandez Forner et al. |
| 7,109,210 B2 * | 9/2006 | Fernandez Forner et al. ............... 514/305 |
| 7,122,558 B2 * | 10/2006 | Prat Quinones et al. ..... 514/305 |
| 7,196,098 B2 | 3/2007 | Fernandez Forner et al. |
| 7,214,687 B2 | 5/2007 | Fernandez Forner et al. |
| RE39,820 E | 9/2007 | Banholzer et al. |
| 7,358,260 B2 | 4/2008 | Fernandez Forner et al. |
| 7,750,023 B2 | 7/2010 | Fernandez Forner et al. |
| 7,776,315 B2 | 8/2010 | Pairet et al. |
| 7,776,879 B2 * | 8/2010 | Buil Albero et al. ......... 514/305 |
| 2002/0122773 A1 | 9/2002 | Pairet et al. |
| 2002/0134538 A1 | 9/2002 | Moreau |
| 2002/0137764 A1 | 9/2002 | Drechsel et al. |
| 2002/0151541 A1 | 10/2002 | Pairet et al. |
| 2002/0179087 A1 | 12/2002 | Bozung et al. |
| 2002/0183292 A1 | 12/2002 | Pairet et al. |
| 2002/0189610 A1 | 12/2002 | Bozung et al. |
| 2002/0193392 A1 | 12/2002 | Schmelzer et al. |
| 2002/0193393 A1 | 12/2002 | Pairet et al. |
| 2003/0018019 A1 | 1/2003 | Meade et al. |
| 2003/0158196 A1 | 8/2003 | Jung et al. |
| 2003/0203925 A1 | 10/2003 | Meade et al. |
| 2004/0024007 A1 | 2/2004 | Pairet et al. |
| 2004/0151770 A1 | 8/2004 | Pairet et al. |
| 2004/0161386 A1 | 8/2004 | Pairet et al. |
| 2004/0176338 A1 | 9/2004 | Pairet et al. |
| 2004/0192675 A1 | 9/2004 | Pairet et al. |
| 2004/0266869 A1 | 12/2004 | Montague et al. |
| 2005/0025718 A1 | 2/2005 | Meade et al. |
| 2005/0026886 A1 | 2/2005 | Meade et al. |
| 2005/0026887 A1 | 2/2005 | Meade et al. |
| 2005/0026948 A1 | 2/2005 | Meade et al. |

(Continued)

FOREIGN PATENT DOCUMENTS
EP          0 418 716         3/1991
(Continued)

OTHER PUBLICATIONS

Kamil Kuča et al., "A general method for the quaternization of N,N-dimethyl benzylamines with long chain n-alkylbromides," Journal of Applied Biomedicine, 2: 195-198 (2004).
International Search Report mailed Nov. 15, 2007, for International Application No. PCT/EP2007/006278 (WO 2008/009397 A1).
U.S. Appl. No. 12/921,892, filed Sep. 10, 2010, Lamarca Casado.
U.S. Appl. No. 12/921,921, filed Sep. 10, 2010, Lamarca Casado.
U.S. Appl. No. 10/047,464, filed Jan. 14, 2002, Fernandez Forner.
U.S. Appl. No. 11/116,777, filed Apr. 28, 2005, Fernandez Forner.
U.S. Appl. No. 10/740,264, filed Dec. 17, 2003, Fernandez Forner.
U.S. Appl. No. 11/325,059, filed Jan. 3, 2006, Fernandez Forner.
U.S. Appl. No. 11/324,919, filed Jan. 3, 2006, Fernandez Forner.
U.S. Appl. No. 11/636,181, filed Dec. 8, 2006, Fernandez Forner.
U.S. Appl. No. 12/074,929, filed Mar. 7, 2008, Fernandez Forner.

(Continued)

*Primary Examiner* — Kamal Saeed
*Assistant Examiner* — Nyeemah A Grazier
(74) *Attorney, Agent, or Firm* — Finnegan, Henderson, Farabow, Garrett & Dunner, LLP

(57) ABSTRACT

This present disclosure relates to a process for manufacturing 3(R)-(2-hydroxy-2,2-dithien-2-ylacetoxy)-1-(3-phenoxypropyl)-1-azoniabicyclo[2.2.2]octane bromide by reacting 2-hydroxy-2,2-dithien-2-ylacetic acid 1-azabicyclo[2.2.2] oct-3(R)yl ester and 3-phenoxypropyl bromide, wherein the reaction takes place in a solvent or mixtures of solvents having a boiling point from 50° C. to 210° C. and chosen from ketones and cyclic ethers.

12 Claims, No Drawings

U.S. PATENT DOCUMENTS

| | | | |
|---|---|---|---|
| 2005/0147564 A1 | 7/2005 | Dreschel et al. | |
| 2005/0209272 A1 | 9/2005 | Fernandez Forner et al. | |
| 2005/0267078 A1 | 12/2005 | Gras Escardo et al. | |
| 2005/0267135 A1 | 12/2005 | Escardo et al. | |
| 2005/0282875 A1* | 12/2005 | Prat Quinones et al. | 514/367 |
| 2005/0288266 A1 | 12/2005 | Gras Escardo et al. | |
| 2006/0057074 A1 | 3/2006 | Meade et al. | |
| 2007/0128125 A1 | 6/2007 | Schmelzer et al. | |
| 2008/0214600 A1* | 9/2008 | Fernandez Forner et al. | 514/305 |
| 2009/0088408 A1 | 4/2009 | Meade et al. | |
| 2010/0234333 A1 | 9/2010 | Fernandez Forner et al. | |
| 2010/0310477 A1 | 12/2010 | Pairet et al. | |
| 2011/0020412 A1 | 1/2011 | Lamarca Casado et al. | |
| 2011/0020454 A1 | 1/2011 | Lamarca Casado | |

FOREIGN PATENT DOCUMENTS

| | | |
|---|---|---|
| EP | 0 424 021 | 3/1994 |
| EP | 0 747 355 | 12/1996 |
| EP | 0 801 067 A1 | 10/1997 |
| EP | 1 087 750 | 4/2004 |
| EP | 1 763 369 | 12/2008 |
| FR | 2012964 | 3/1970 |
| GB | 1219606 | 1/1971 |
| WO | WO 91/04252 | 4/1991 |
| WO | WO 92/04345 | 3/1992 |
| WO | WO 96/32150 | 10/1996 |
| WO | WO 00/47200 | 8/2000 |
| WO | WO 01/04118 | 1/2001 |
| WO | WO 01/04118 A2 | 1/2001 |
| WO | WO 01/50080 | 7/2001 |
| WO | WO 01/78736 | 10/2001 |
| WO | WO 01/78739 | 10/2001 |
| WO | WO 01/78741 | 10/2001 |
| WO | WO 01/78743 | 10/2001 |
| WO | WO 02/36106 | 5/2002 |
| WO | WO 02/38154 | 5/2002 |
| WO | WO 02/47667 | 6/2002 |
| WO | WO 02/051841 | 7/2002 |
| WO | WO 02/053564 | 7/2002 |
| WO | WO 02/060532 | 8/2002 |
| WO | WO 02/060533 | 8/2002 |
| WO | WO 03/000241 | 1/2003 |
| WO | WO 03/087094 A1 | 10/2003 |
| WO | WO 03/097613 | 11/2003 |
| WO | WO 2004/043966 | 5/2004 |
| WO | WO 2004058729 | 7/2004 |
| WO | WO 2005/014005 | 2/2005 |
| WO | WO 2005/049581 | 6/2005 |
| WO | WO 2005/090342 A1 | 9/2005 |
| WO | WO 2005/115462 | 12/2005 |
| WO | WO 2005/115466 | 12/2005 |
| WO | WO 2005/115467 | 12/2005 |
| WO | WO 2009/112274 | 9/2009 |

OTHER PUBLICATIONS

U.S. Appl. No. 12/787,772, filed May 26, 2010, Fernandez Forner.
U.S. Appl. No. 11/141,427, filed May 31, 2005, Gras Escardo.
U.S. Appl. No. 11/141,428, filed May 31, 2005, Gras Escardo.
U.S. Appl. No. 11/141,169, filed May 31, 2005, Gras Escardo.
U.S. Appl. No. 10/892,033, filed Jul. 15, 2004, Meade.
6001 chemical abstracts, Columbus, OH, US, vol. 104(19). XP-002128290, p. 659 (1985).
Appeal Brief in U.S. Appl. No. 10/892,033 dated Aug. 30, 2010.
Atrovent® (ipratropium bromide) Inhalation Solution Prescribing Information, Boehringer Ingelheim International GmbH 830885-R, Revised Oct. 1998.
Atrovent® Aerosol Prescribing Information, Boehringer Ingelheim International GmbH 10001403US/1, 10001403/01, Revised Mar. 27, 2002.
Ayres, JG et al. Thorax 52(Supp 1): S1-S21 (1997).
BTS Guidelines for the Management of Chronic Obstructive Pulmonary Disease, the COPD Guidelines Group of the Standards of Care Committee of the BTS, Boehringer Ingelheim Ltd., Thorax, (1997).
Burtner, R. et al. Antispasmodics II. Basic Esters of Some Polynuclear Carboxylic Acids, J. Am. Chem. Soc. 65: 1582-1585 (1943).
Cohen, VI et al. "Synthesis and Receptor Affinities for New 3-Quinuclidinyl a-Heteroaryl-a-aryl-a-Hydroxyacetates,". J. Pharm. Sciences, 81: 326-329 (1992).
Combivent, Inhalation Aerosol Prescribing Information, Boehringer Ingelheim International GmbH, 10000291/03, revised Sep. 2001.
Costain, D. et al. "Guidelines for Management of Asthma in Adults: I-Chronic Persistent Asthma," Br. Med. J. 301: 651-653 (1990).
Davis, MA et al. "New Psychotropic Agents VI, Basic Esters of 5-Hydroxydibenzo[a,d]cycloheptadiene-5-carboxylic acid," J. Med. Chem 6: 513-51 (1963).
Davis, MA et al. "Anticonvulsants I. Dibenzo[a,d]cycloheptadiene-5-carboxamide and Related Compounds," J. Med. Chem 7: 88-94 (1964)).
Eglen, RM et al. "Muscarinic Receptor Subtypes: Pharmacology and Therapeutic Potential," DN & P, 10(8): 462-469 (Oct. 1997).
Foye, et al. Principles of Medicinal Chemistry, 4th Edition, pp. 338-340 (1995).
Godoviko, et al. "Synthesis and Receptor Affinities of New 3-Quinuclidinyl a-Heteroaryl-aaryl-ahydroxyacetates," Journal of Pharmaceutical Sciences, 81(4): 326-329 (1992).
Heacock, RA et al., "Materials and Methods," The Annals of Applied Biology, Marsh RW and Thomas, I, eds, Cambirdge at the University Press, vol. 46, pp. 356-366 (1958).
Hancox, RJ et al. "Randomised trial of an inhaled B2 agonist, inhaled corticosteroids and their combination in the treatment of asthma," Thorax, 54: 482-487 (1999).
International Search Report for International Application No. PCT/EP2009/001831, dated Jul. 2, 2010.
International Search Report for International Application No. PCT/EP2009/001832, dated Jul. 5, 2010.
Kumazawa, T et al. "Inhibitors of Acyl-CoA Cholesterol Acyltransferase 1. Synthesis and Hypocholesterolemic Activity of Dibenz[b,e]oxepin-11carboxanilides," J. Med. Chem 37(6): 804-810 (1994).
Larsson, L et al. "The Hydrogen Bond Condition in Some Anticholinergic Esters of Glycolic Acids I," Acta. Pharma. Suec. 11(3): 304-308 (1974).
Martin, L. "Drugs for Asthma/COPD—A Medical Primer for Physicians," http://www.lakesidepress.com/pulmonary/Asthma-Rx.html (updated Feb. 1999).
Martindale, The Complete Drug Reference, Kathleen Parfitt ed., 32nd ed., pp. 745-747 (1999).
May, EL et al. "Studies in the Anthracene Series V. A Novel Rearrangement in the Reaction of Halomethyl Ketones with Secondary Amines," J. Am. Chem. Soc. 70: 1077-1079 (1948).
Merck Manual of Diagnosis and Therapy, Robert Berkow ed., 16th Edition, p. 646-657 (1992).
Meyers, AI et al. "Resolution of a-Substituted Mandelic Acids via Chiral Oxazolines Using Pressurized Chromatography," J. Org. Chem. 45(14): 2912-2914(1980).
Naronha-Blob, L et al. Stereoselective antimuscarininc effects of 3-quinuclidinyl atrolactate and 3-quinuclidinyl xanthene-9-carboxylate, 211:97-103 (1992).
Nishimura, et al. "Additive effect of oxitropium bromide in combination with inhaled corticosteroids in the treatment of elderly patients with chronic asthma," Allerology International 48: 85-88 (1999).
Notice of Allowance dated Mar. 30, 2005 in U.S. Appl. No. 10/740,264.
Notice of Allowance dated Dec. 21, 2005 in U.S. Appl. No. 11/116,777.
Notice of Allowance dated Sep. 13, 2006 in U.S. Appl. No. 11/325,059.
Notice of Allowance dated Jan. 9, 2007 in U.S. Appl. No. 11/324,919.
Notice of Allowance dated Nov. 23, 2007 in U.S. Appl. No. 11/636,181.
Notice of Allowance dated Feb. 26, 2010, in U.S. Appl. No. 12/074,929.
Notice of Allowance dated Jan. 10, 2011 in U.S. Appl. No. 12/787,772.
Nyberg, K. et al. "Investigations of Dithienylglycolic Esters," Acta. Chem. Scand. 24: 1590-1596 (1970).
Office Action dated Apr. 22, 2004 in U.S. Appl. No. 10/740,264.
Office Action dated Jul. 22, 2004 in U.S. Appl. No. 10/740,264.

Office Action dated Sep. 19, 2005 in U.S. Appl. No. 11/116,777.
Office Action dated Mar. 14, 2006 in U.S. Appl. No. 11/325,059.
Office Action dated Apr. 28, 2006 in U.S. Appl. No. 11/324,919.
Office Action dated Jul. 6, 2007 in U.S. Appl. No. 11/636,181.
Office Action dated Mar. 4, 2009 in U.S. Appl. No. 12/074,929.
Office Action dated Oct. 7, 2009 in U.S. Appl. No. 12/074,929.
Office Action dated Oct. 19, 2010, in U.S. Appl. No. 12/787,772.
Office Action dated Oct. 2, 2007 in U.S. Appl. No. 10/892,033.
Rang, HP et al. "Pharmacology," Churchill Livingston Inc., pp. 358-361 (1995).
Ringdahl, R. et al. "Facile Preparation of the Enantiomers of 3-Acetoxyquinuclidinol," Acta Pharm Suec. 16: 281-283 (1979).
Serafin, W. "Drugs Used in the Treatment of Asthma," Goodman ^ Gilman's The Pharmacological Basis of Therapeutics, Chapter 28 , Joel G. Hardman et al eds, 9th Edition, pp. 659-682 (1996).
Sestanj, K. "A Facile Formation of Dibenzo[a,b] cycloheptenylium Ion by Decarbonylation Color Reactions of the Cyheptaminde Metabolites," Can. J. Chem. 49: 664-665 (1971).

Schelfhout, VJ et al. Activity of LAS 34273, A New Long Acting Anticholinergic Antagonist, in COPD Patients, poster, ATS 2003-99th International Conference, May 2003.
Schelfhout, VJ et al. "Activity of LAS 34273, a new long acting anticholinergic antagonist," ATS 2003-99th International Conference, May 2004.
Spirva®Handhihaler® Prescribing Information, Boehringer Ingelheim International GmbH, 59873/US/2, Sep. 2004.
Ueda, I. "The Rearrangement of 10-Bromo-10, 11-Dihydrodibenzo[b,f]thiepin-11-one and Related Compounds in an Alkaline Solution," Bulletin of the Chemical Socieyt of Japan, 48(4): 2306-2309 (1975).
Waelbroek, M. et al. "Binding of Selective Antagonists to Four Muscarinic Receptors (M1 to M4) in Rat Forebrain," Mol. Pharmacol. 38:267-273 (1990).

* cited by examiner

PROCESS FOR MANUFACTURING 3(R)-(2-HYDROXY-2,2-DITHIEN-2-YLACETOXY)-1-(3-PHENOXYPROPYL)-1-AZONIABICYCLO[2.2.2]OCTANE BROMIDE

This application is a national stage filing under 35 U.S.C. §371 of International Application No. PCT/EP2007/006278 filed on 16 Jul. 2007, which claims priority of Spanish Patent Application No. P200601951, filed on 21 Jul. 2006. The contents of both applications are incorporated herein by reference.

The present invention relates to a process for the manufacture of 3(R)-(2-hydroxy-2,2-dithien-2-ylacetoxy)-1-(3-phenoxypropyl)-1-azoniabicyclo[2.2.2]octane.

This compound as well as a process for its manufacture are described in WO 01/04118 A2.

The inventors have now unexpectedly found that by proper selection of the reaction conditions the process described in WO 01/04118 A2 can be optimized enabling to decrease the reaction time and the quantity of solvents and alkylating reactant used while increasing the yield and maintaining the level of impurities.

These objectives can be achieved by carrying out the quaternization reaction between 2-hydroxy-2,2-dithien-2-ylacetic acid 1-azabicyclo[2.2.2]oct-3(R)yl ester and 3-phenoxypropyl bromide in a solvent or mixture of solvents having a boiling point of between 50 and 210° C. and selected from the group consisting of ketones and cyclic ethers. In an advantageous embodiment of the present invention a single solvent is used.

The following are some examples of ketones or cyclic ethers that can be used as solvents for carrying out the invention: acetone, methyl ethyl ketone, methyl isobutyl ketone, phenyl methyl ketone, cyclopentanone dioxane, tetrahydrofurane, ethyltetrahydrofurane. Preferred solvents are selected from the group consisting of acetone, dioxane or tetrahydrofurane. A particularly preferred solvent is tetrahydrofurane.

In particular, it has been advantageous to use an equivalent ratio of 3-phenoxypropyl bromide to 2-hydroxy-2,2-dithien-2-ylacetic acid 1-azabicyclo[2.2.2]oct-3(R)yl ester in the range of 1.0 to 3.0, more preferably between 1.1 and 1.5, most preferably between 1.2 and 1.3.

In a further preferred embodiment the 2-hydroxy-2,2-dithien-2-ylacetic acid 1-azabicyclo[2.2.2]oct-3(R)yl ester is suspended (or dissolved) in a volume of solvent or solvent mixture comprised between 1.7 and 7 liters of solvent(s) per mol of 2-hydroxy-2,2-dithien-2-ylacetic acid 1-azabicyclo[2.2.2]oct-3(R)yl ester. More preferably the ester is suspended (or dissolved) in a volume of solvent comprised between 1 and 7, preferably between 2 and 4 liters per mol of ester.

Under these conditions it has proven adequate to allow the mixture to react for a time period not exceeding 24 hours, preferably not longer than 12 hours more preferably not longer than 9 hours and most preferably up to 6 hours.

Particularly good results are obtained when 2-hydroxy-2,2-dithien-2-ylacetic acid 1-azabicyclo[2.2.2]oct-3(R)yl ester is suspended in 2 to 4 l of tetrahydrofurane per mole of 2-hydroxy-2,2-dithien-2-ylacetic acid 1-azabicyclo[2.2.2]oct-3(R)yl ester, from 1.2 to 1.3 equivalents of 3-phenoxypropyl bromide are added to the resulting suspension and the mixture is stirred for not more than 9 hours, preferably not more than 6 h at reflux in an inert atmosphere.

The following examples show illustrative methods for preparing compounds according to the present invention, and are not intended to limit the scope of the invention.

EXPERIMENTAL SECTION

Comparative Example 1

According to WO 01/04118

0.6 mmol of 2-hydroxy-2,2-dithien-2-ylacetic acid 1-azabicyclo[2.2.2]oct-3(R)yl ester are suspended in 4 ml of $CH_3CN$ and 6 ml of $CHCl_3$. 0.48 ml of 3-phenoxypropyl bromide were added to the resulting suspension and the mixture was stirred for 72 h at room temperature in an inert atmosphere. The solvents were subsequently evaporated to yield (90%) of 3(R)-(2-hydroxy-2,2-dithien-2-ylacetoxy)-1-(3-phenoxypropyl)-1-azoniabicyclo[2.2.2]octane bromide. The product is isolated by filtration at room temperature and the level of 3-phenoxypropyl bromide is determined to be 117 ppm.

Examples 2 to 8

The moles of 2-hydroxy-2,2-dithien-2-ylacetic acid 1-azabicyclo[2.2.2]oct-3(R)yl ester indicated in column B were suspended in the amount (column E) of the solvent indicated in column D. Then, the amount of 3-phenoxypropyl bromide resulting from multiplying column B by column C was added to the resulting suspension and the mixture was stirred for 6 h at reflux in an inert atmosphere. The solvents were subsequently evaporated to yield 3(R)-(2-hydroxy-2,2-dithien-2-ylacetoxy)-1-(3-phenoxypropyl)-1-azoniabicyclo [2.2.2]octane bromide. The product was isolated by filtration at room temperature and both the yield and the level of 3-phenoxypropyl bromide were determined and indicated in columns F and G, respectively.

The following table summarizes the results of comparative example 1 and examples 2 to 8 of the present invention.

TABLE I

| A Ex | B Amount of 2-hydroxy-2,2-dithien-2-ylacetic acid 1-azabicyclo[2.2.2]oct-3(R)yl ester (mmoles) | C Ratio (Eq) of 3-phenoxypropyl bromide to 2-hydroxy-2,2-dithien-2-ylacetic acid 1-azabicyclo[2.2.2]oct-3(R)yl ester | D Solvent | E Amount of solvent (l/mol) | F Yield (%) | G Amount of 3-phenoxypropyl bromide (ppm) |
|---|---|---|---|---|---|---|
| 1* | 0.6 | 5.0 | $CH_3CN/CHCl_3$ | 16.7 | 90 | 117 |
| 2 | 71.53 | 1.25 | THF | 2.1 | 95.0 | 148 |
| 3 | 71.53 | 1.10 | THF | 2.1 | 92.4 | 60 |
| 4 | 71.53 | 1.10 | Acetone | 2.1 | 95.3 | 152 |
| 5 | 71.53 | 1.25 | Acetone | 2.1 | 98.7 | 173 |
| 6 | 71.53 | 1.25 | Acetone | 7.0 | 93.7 | 60 |

TABLE I-continued

| Ex | A<br>Amount of 2-hydroxy-2,2-dithien-2-ylacetic acid 1-azabicyclo[2.2.2]oct-3(R)yl ester (mmoles) | B<br>Ratio (Eq) of 3-phenoxypropyl bromide to 2-hydroxy-2,2-dithien-2-ylacetic acid 1-azabicyclo[2.2.2]oct-3(R)yl ester | C<br>Solvent | D<br>Amount of solvent (l/mol) | E<br>Yield (%) | F<br>Amount of 3-phenoxy-propyl bromide (ppm) |
|---|---|---|---|---|---|---|
| 7 | 14.31 | 1.50 | Methyl ethyl ketone | 2.1 | 96.9 | 304 |
| 8 | 14.31 | 1.50 | Methyl isobutyl ketone | 3.5 | 94.7 | 410 |
| 9 | 42.92 | 1.25 | Dioxane | 2.1 | 98.2 | 31 |
| 10 | 71.53 | 1.25 | Methyl THF | 2.1 | 96.7 | 212 |
| 11 | 42.92 | 1.25 | Acetophenone | 2.1 | 98.5 | 53 |
| 12 | 42.92 | 1.25 | Cyclopentanone | 2.1 | 94.4 | 167 |

*The reaction of comparative example 1 was carried out by stirring at room temperature during 72 hours As can be seen from the results of table I show that the method of the present invention allows shortening the reaction time and reducing the quantity of 3-phenoxypropyl bromide employed while simultaneously increasing the yield and yet maintaining the amount of the genotoxic 3-phenoxypropyl bromide impurity at an acceptable level of below 500 ppm.

The invention claimed is:

1. A process for manufacturing 3(R)-(2-hydroxy-2,2-dithien-2-ylacetoxy)-1-(3-phenoxypropyl)-1-azoniabicyclo[2.2.2]octane bromide comprising reacting 2-hydroxy-2,2-dithien-2-ylacetic acid 1-azabicyclo[2.2.2]oct-3(R)yl ester and 3-phenoxypropyl bromide, wherein the reaction takes place in a solvent or mixtures of solvents having a boiling point from 50° C. to 210° C., and chosen from ketones and cyclic ethers.

2. A process according to claim 1, wherein the equivalent ratio of 3-phenoxypropyl bromide to 2-hydroxy-2,2-dithien-2-ylacetic acid 1-azabicyclo[2.2.2]oct-3(R)yl ester is in the range from 1.0 to 3.0.

3. A process according to claim 2, wherein the equivalent ratio is in the range from 1.1 to 1.5.

4. A process according to claim 2, wherein the equivalent ratio is in the range from 1.2 to 1.3.

5. A process according to claim 1, wherein 2-hydroxy-2,2-dithien-2-ylacetic acid 1-azabicyclo[2.2.2]oct-3(R)yl ester is suspended or dissolved in a volume of solvent or solvent mixture comprising from 1.7 to 7 liters of solvent(s) per mol of 2-hydroxy-2,2-dithien-2-ylacetic acid 1-azabicyclo[2.2.2]oct-3(R)yl ester.

6. A process according to claim 5, wherein the volume of solvent comprises from 2 to 4 liters per mol of 2-hydroxy-2,2-dithien-2-ylacetic acid 1-azabicyclo[2.2.2]oct-3(R)yl ester.

7. A process according to claim 1, wherein the solvent is chosen from acetone, dioxane and tetrahydrofurane.

8. A process according to claim 7, wherein the solvent is tetrahydrofurane.

9. A process according to claim 1, wherein the mixture is allowed to react for a time period not exceeding 24 hours.

10. A process according to claim 9, wherein the time period is not more than 12 hours.

11. A process according to claim 10, wherein the time period is not more than 9 hours.

12. A process according to claim 11, wherein the time period is not more than 6 hours.

* * * * *